United States Patent
Ryan et al.

(10) Patent No.: US 9,264,649 B2
(45) Date of Patent: Feb. 16, 2016

(54) MEDICAL VIDEO COMMUNICATION SYSTEMS AND METHODS

(71) Applicant: Koninklijke Philips Electronics N.V., Eindhoven (NL)

(72) Inventors: John C. Ryan, Boston, MA (US); Ashik Uzzaman, Freemont, CA (US)

(73) Assignee: Koninklijke Philips N.V., Eindhoven (NL)

( * ) Notice: Subject to any disclaimer, the term of this patent is extended or adjusted under 35 U.S.C. 154(b) by 98 days.

(21) Appl. No.: 13/756,626

(22) Filed: Feb. 1, 2013

(65) Prior Publication Data

US 2013/0148942 A1     Jun. 13, 2013

Related U.S. Application Data

(62) Division of application No. 12/525,221, filed on Jul. 30, 2009, now Pat. No. 8,390,694.

(51) Int. Cl.
*H04N 5/228* (2006.01)
*H04N 5/765* (2006.01)
*A61B 5/00* (2006.01)
*G06F 19/00* (2011.01)

(52) U.S. Cl.
CPC ....... *H04N 5/765* (2013.01); *A61B 5/00* (2013.01); *G06F 19/30* (2013.01)

(58) Field of Classification Search
CPC ....... H04N 5/765; H04N 7/141; H04N 7/147; A61B 5/00
USPC ............... 348/222.1, 333.02, 335, 340
See application file for complete search history.

(56) References Cited

U.S. PATENT DOCUMENTS

| | | |
|---|---|---|
| 6,014,432 A | 1/2000 | Modney |
| 6,039,688 A | 3/2000 | Douglas et al. |

(Continued)

FOREIGN PATENT DOCUMENTS

| | | |
|---|---|---|
| EP | 1617361 A1 | 1/2006 |
| GB | 2286312 A | 8/1995 |

(Continued)

OTHER PUBLICATIONS

Cybernet Systems Corporation; Cybernet Medical: The MedStar System; Oct. 17, 2006; www.cybernetmedical.com/files/medstar-case-mail.pdf.

*Primary Examiner* — Yogesh Aggarwal

(57) ABSTRACT

A medical communication system includes a plurality of end-user audio/video recording and playback devices (40) disposed with recipients of medical assistance, and a medical server (10) configured to receive audio/video messages (90') generated by the end-user audio/video devices and to generate and transmit audio/video responses (94) to targeted end-user audio/video devices. The medical server includes an audio/video recording and playback device (12) configured to playback received audio/video messages and to record audio/video responses, and the end user audio/video recording and playback devices are configured to playback audio/video responses (94') received from the server. In some embodiments, each end-user audio/video device includes: a video recording lens (62); a microphone (64); and an automatic lens cover (63) arranged to physically block the video recording lens except during recording of audio/video content. In some embodiments, each end-user audio/video device includes a consumer entertainment device (50, 52).

18 Claims, 5 Drawing Sheets

(56) References Cited

U.S. PATENT DOCUMENTS

Figure 1:
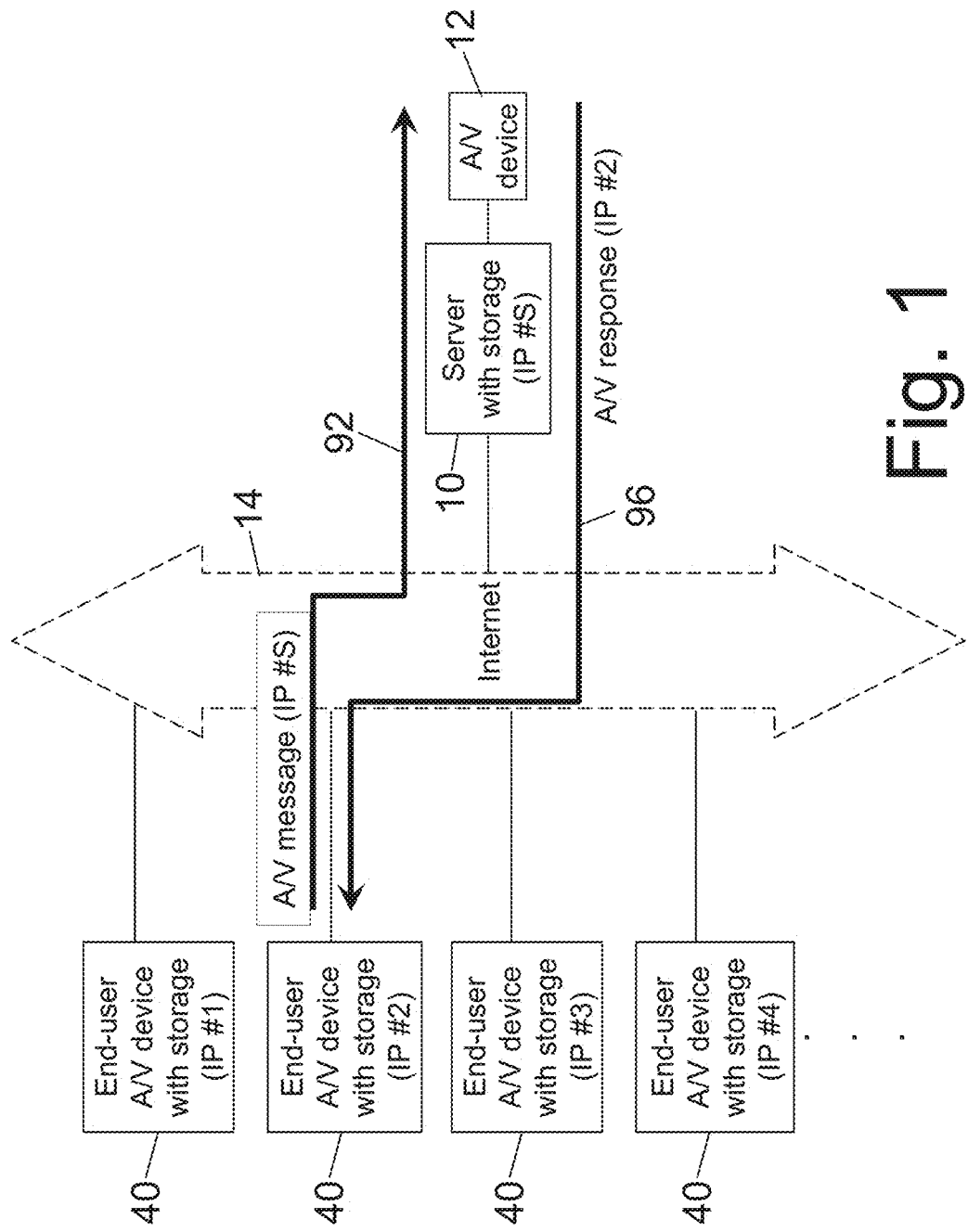

| | | | |
|---|---|---|---|
| 6,515,705 B1 | 2/2003 | Fumio et al. | 348/375 |
| 6,757,413 B1 | 6/2004 | LeMahieu | |
| 6,970,098 B1 | 11/2005 | Adams et al. | |
| 2001/0052019 A1 | 12/2001 | Walters et al. | |
| 2002/0116221 A1 | 8/2002 | Fields et al. | |
| 2002/0186243 A1 | 12/2002 | Ellis et al. | 345/753 |
| 2003/0140106 A1 | 7/2003 | Raguseo | |
| 2003/0177193 A1 | 9/2003 | Budge et al. | |
| 2004/0250210 A1 | 12/2004 | Huang et al. | |
| 2006/0030360 A1 | 2/2006 | Yeh | 455/557 |
| 2006/0061962 A1 | 3/2006 | Oakley | |
| 2006/0064645 A1 | 3/2006 | Neven et al. | |
| 2007/0050294 A1 | 3/2007 | Trottier et al. | 705/50 |
| 2008/0077881 A1* | 3/2008 | Gilley et al. | 715/810 |
| 2008/0141147 A1 | 6/2008 | Buhrke et al. | 715/757 |
| 2009/0009356 A1* | 1/2009 | Stepanian | 340/825.24 |
| 2013/0182834 A1 | 7/2013 | Lauffer | |

FOREIGN PATENT DOCUMENTS

| | | |
|---|---|---|
| JP | 099123 A | 1/1997 |
| JP | 2002232971 A | 8/2002 |
| JP | 2002540511 A | 11/2002 |
| JP | 2003044584 A | 2/2003 |
| JP | 2004240553 A | 8/2004 |
| WO | 0203284 A1 | 1/2002 |
| WO | 2004038978 A2 | 5/2004 |
| WO | 2006092810 A2 | 9/2006 |
| WO | 2006138680 A1 | 12/2006 |

* cited by examiner

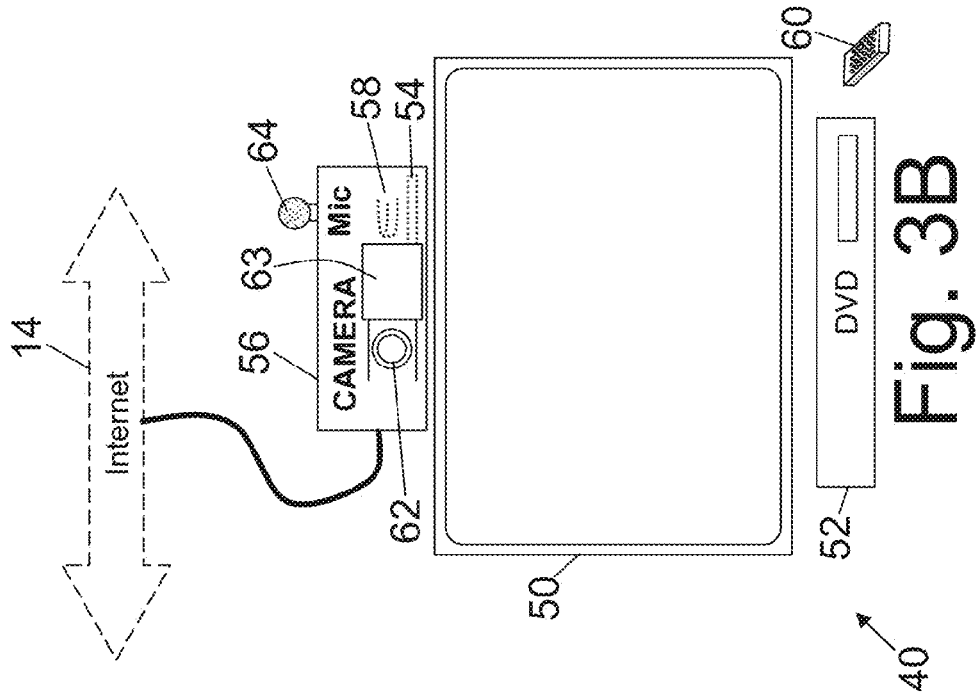
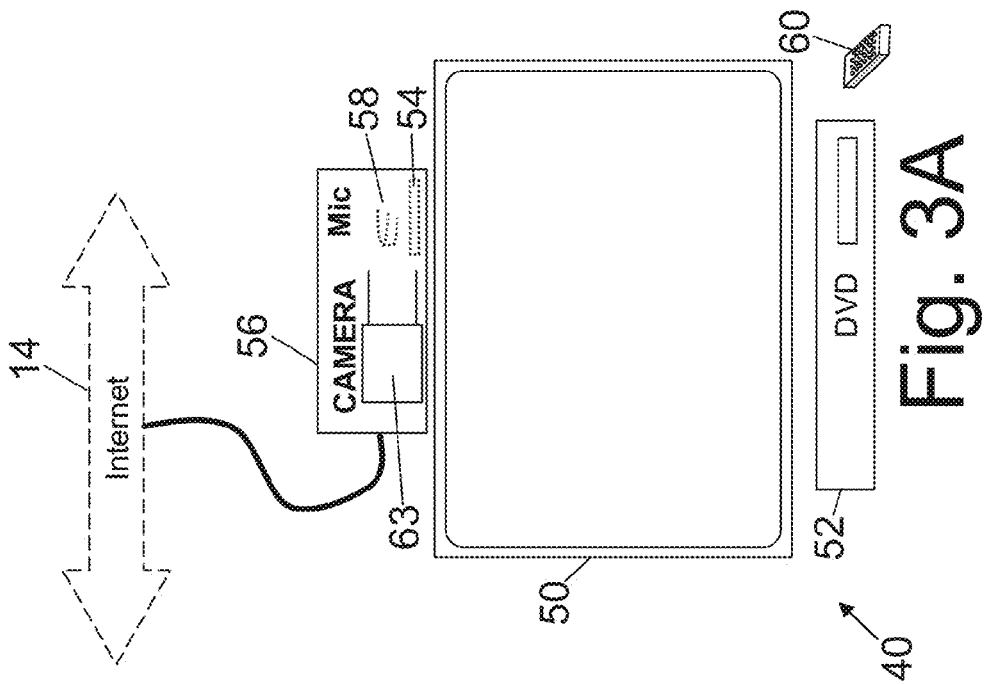

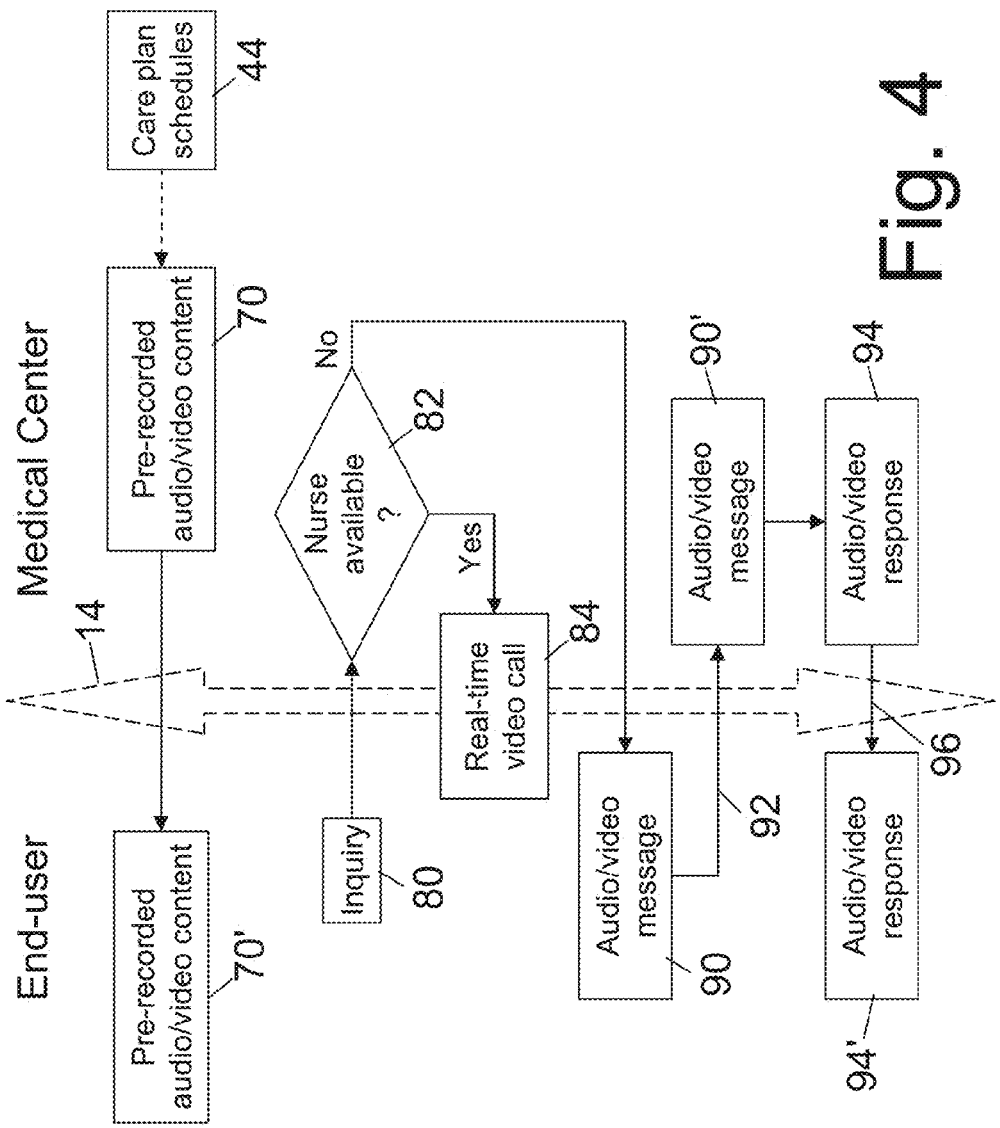

MEDICAL VIDEO COMMUNICATION SYSTEMS AND METHODS

This application is a divisional of U.S. application Ser. No. 12/525,221 filed Jul. 30, 2009 and since issued as U.S. Pat. No. 8,390,694 on Mar. 5, 2013, which is a National Stage of international Application No. PCT/IB2008/050275 filed Jan. 25, 2008 which claims the benefit of U.S. provisional application Ser. No. 60/887,823 filed Feb. 2, 2007. This application claims the benefit of U.S. provisional application Ser. No. 60/887,823 filed Feb. 2, 2007, which is incorporated herein by reference.

The following relates to the medical arts. It finds application in treatment, care, monitoring, and so forth of patients in homes, apartments, nursing care facilities, hospices, hospitals, treatment centers, and so forth.

Maintenance of open lines of communication between medical professionals and chronically ill patients is a recognized factor in effective medical treatment. Good communication generally correlates with a more positive medical outcome. Poor communication can adversely affect the patient in numerous ways. The patient's self-care (e.g., taking medications in a timely manner, maintaining exercise and diet regimens, and so forth) can be adversely affected though patient misunderstanding regarding dosages or other therapy aspects. Poor communication can also adversely affect the patient's psychological health, for example leading to patient depression, apathy, or so forth. Poor communication can also result in the patient not reporting medically probative physiological or psychological symptoms, or loss of such reports in the communication chain. Where communication is limited to telephone or writing, non-verbal communication such as gestures, overall demeanor, and so forth are lost.

Although open lines of communication have recognized benefits, there are also disadvantages. Medical professionals are valuable specialized caregivers. Having a doctor constantly fielding telephone calls or other inquiries from patients is not an effective use of this resource. This is especially true where, as is often the case, the patient is lonely and primarily wants to talk, but does not have medically pertinent information or questions. Such psychological needs, while important, are better satisfied though the intervention of psychologists, case workers, or other personnel.

In an attempt to provide effective communication while not overburdening medical personnel, a structured communication paradigm is typically used. For example, telephone calls to a doctor's office are typically fielded by a receptionist who screens the calls and takes messages where appropriate. The doctor then receives messages of importance, and relays information back to the patient either via the receptionist or through a direct return telephone call to the patient. These approaches provide numerous opportunities for miscommunication or lost communication, and typically leave the patient feeling that the doctor has little interest in his or her medical condition.

Another structured communication approach is the medical form. Such forms are ubiquitous in medical care settings, and typically comprise a questionnaire of medical or medically related questions for the patient to fill out. For home care, it is known to transmit such questionnaires electronically to the patient, e.g. over a broadband Internet connection. Using a questionnaire has the advantage of providing a written record of information, but the quality of that information can be compromised by patient misunderstandings regarding the questions, or patient apathy leading to incomplete or incorrect answers. Moreover, patients typically do not like filling out forms, and again feel that the doctor is avoiding them.

Scheduled visits to the doctor's office or to other medical facilities provide another line of communication. Advantageously, the patient and doctor can engage in personal two-way conversation during such visits. However, this approach is time-consuming for the doctor, and scheduled visits are typically infrequent and short, sometimes being limited to fifteen minutes or less per visit, with a scheduled visit every month, every six months, or at some other infrequent interval. Thus, scheduled visits are insufficient to maintain an open line of communication with the patient.

A television-based interactive healthcare platform called Motiva® has been developed by Koninklijke Philips Electronics N.V. (Eindhoven, Netherlands). This system transmits scheduled motivational, instructional, or other medically related audio/video content to the patient, and can receive biometric measurement data, survey responses, and so forth from the patient. The content is scheduled by a nurse or other caregiver, and is personalized for each patient.

A problem with the scheduled communication paradigm is that medical problems and concerns generally do not follow a pre-determined schedule. A patient may experience a new symptom or other medical situation calling for communication with a nurse, physician or other medical person at any time.

Heretofore, the principal apparatus for addressing such unscheduled issues has been the telephone. The patient telephones the doctor's office during business hours, or perhaps telephones a nurse call line having twenty-four availability for after-hours usage. Some such telephonic lines of communication are intended for emergency situations only. Even where a telephonic line of communication is intended for broader purposes, such as to address more routine patient questions, it is not uncommon for a patient to avoid using them unless and until an acute medical problem develops. The audio-only nature of telephonic communication leaves the patient unfulfilled. Additionally, the spontaneous nature of telephonic communication can result in the responding nurse seeming to be curt or unsympathetic to the patient.

The following provides a new and improved apparatuses and methods which overcome the above-referenced problems and others.

In accordance with one aspect, a medical communication system is disclosed, comprising: a plurality of patient audio/video recording and playback devices disposed with patients receiving medical assistance; and a medical server configured to receive audio/video messages generated by the patient audio/video devices and to generate and transmit audio/video responses to targeted patient audio/video devices, the medical server including an audio/video recording and playback device configured to playback received audio/video messages and to record audio/video responses, the patient audio/video recording and playback devices being configured to playback audio/video responses received from the server.

In accordance with another aspect, an audio/video recording and playback device is disclosed, comprising: a video recording lens; a microphone; and an automatic lens cover arranged to physically block the video recording lens except during recording of audio/video content.

In accordance with another aspect, an apparatus is disclosed, comprising: a handheld remote controller for controlling a television, DVD, set top box, or other electronic device, the handheld remote controller including tactile controls for entering control commands; a built-in microphone built into the handheld remote controller; and a transmitter for transmitting audio picked up by the built-in microphone from the handheld remote controller.

In accordance with another aspect, a medical communication method is disclosed that is operative in conjunction with a medical communication network including patient audio/video recording and playback devices disposed with associated patients and a medical server storing care plan schedules for the patients and configured to transmit audio/video content to the audio/video recording and playback devices of targeted patients according to the care plan schedules. The medical communication method includes: initiating via one of the end user audio video recording and playback devices a query transmitted over the medical communication network to the medical server and addressed to one or more medical professionals; and generating a two way real time audio/video call between the end user associated with the initiating end user audio/video recording and playback device and an available medical professional.

In accordance with another aspect, a medical communication system is disclosed, comprising: a camera; local storage; and a processor configured to (i) play audio/video content in cooperation with a consumer entertainment device, (ii) record audio/video content in cooperation with the camera, (iii) store audio/video content at the local storage; (iv) send to and receive from the medical server audio/video messages and responses over a communication link, and (v) provide a graphical user interface in cooperation with the consumer entertainment device enabling at least selective playback of pre-recorded audio/video content received from the medical server, recording and sending audio/video messages to the medical server, and receiving and playing audio/video responses from the medical server.

In accordance with another aspect, a medical communication method is disclosed, comprising: pushing audio/video content from a medical server to the residence of an end user via a communication pathway; playing the pushed audio/video content on a television disposed in the residence of the end user; recording an audio/video message at the instigation of the end user; transmitting the recorded audio/video message from the end user to the medical server via the same communication pathway across which the audio/video content is pushed; receiving an audio/video response from the medical server via the same communication pathway across which the audio/video content is pushed; and playing the received audio/video response on the television viewable by the end user.

One advantage resides in improved communication between medical professionals and chronically ill patients.

Another advantage resides in improved patient attitudes and outcomes.

Another advantage resides in reduced health care costs.

Still further advantages of the present invention will be appreciated to those of ordinary skill in the art upon reading and understand the following detailed description.

FIG. 1 diagrammatically shows an illustrative medical communication system.

Figure 2:
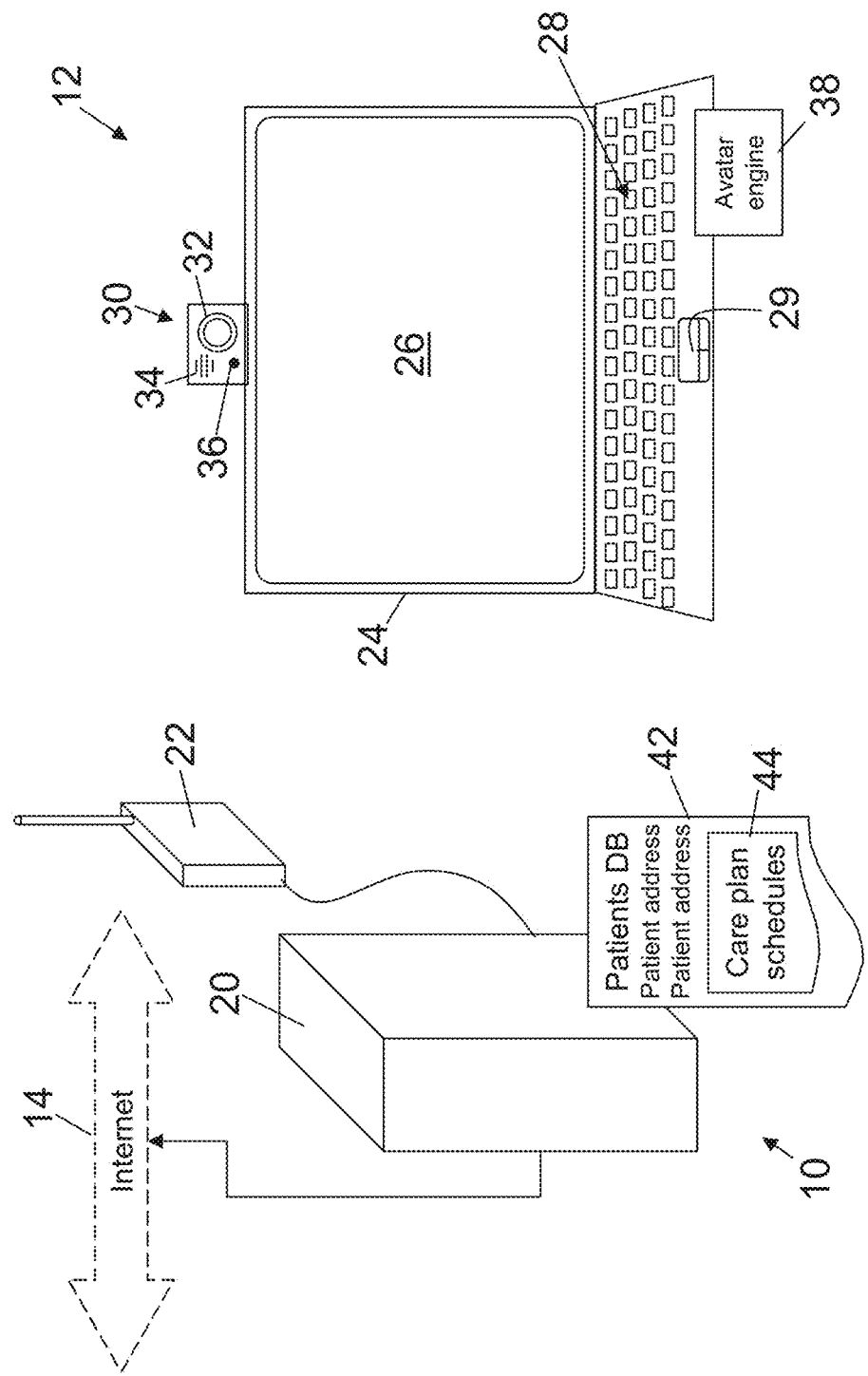

FIG. 2 diagrammatically shows an illustrative embodiment of the medical server of the illustrative medical communication system of FIG. 1.

FIGS. 3A and 3B diagrammatically shows an illustrative embodiment of one of the end-user audio/video recording and playback devices of the illustrative medical communication system of FIG. 1. More particularly:

FIG. 3A shows the illustrative end-user device when it is not recording audio/video content; and FIG. 3B shows the illustrative end-user device when it is recording audio/video content.

FIG. 4 diagrammatically shows illustrative audio/video content, message and response transfers across the illustrative medical communication system of FIG. 1.

Figure 5:
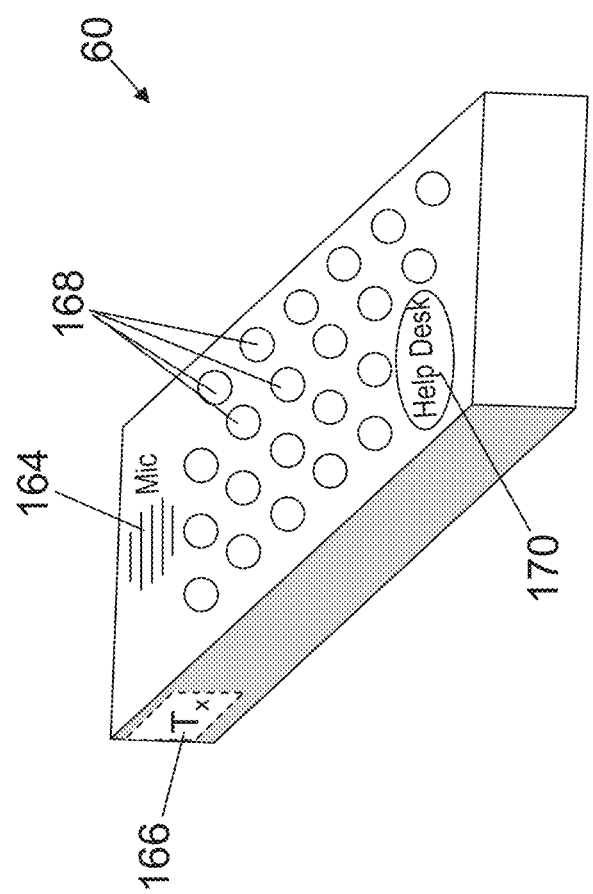

FIG. 5 diagrammatically shows a perspective view of a handheld remote controller including a microphone.

With reference to FIG. 1, a medical communication system includes a medical server 10 having storage and including an audio/video recording and playback device 12. The medical server 10 is operatively connected with the Internet 14 to send and receive data in an addressed manner. For example, at an Internet Protocol/Transmission Control Protocol (IP/TCP) level, the medical server is addressed using its Internet Protocol (IP) address, diagrammatically indicated as "IP #S" in FIG. 1. At the hypertext transfer protocol level (http, i.e., the world wide web level), the server can be suitably identified by a uniform resource locator (URL) such as, for example, "http://www.medserver.com/", which is converted to an IP address using a Domain Name System or Service or Server (DNS) lookup. In some embodiments, the IP address changes dynamically, and a URL and suitably updated DNS provides the conversion to IP address. While the illustrated embodiment uses the Internet 14 for intercommunication, it is also contemplated to use another network, such as an Ethernet or wireless Ethernet. For Ethernet-based communication, a Media Access Control (MAC) address is suitably used. The communication pathway may include multiple communication media, such as the Internet 14 with an Ethernet link at the server end in the illustrated embodiment.

With reference to FIG. 2, an illustrative medical server 10 includes a central processing unit (CPU) 20 that contains or accesses storage and supports a wireless local area network (WLAN or WiFi, for example), a wired network such as a wired Ethernet, or some combination of wired and wireless local networking. In the illustrative embodiment of FIG. 2, a WLAN is accessed at wireless access points such as an illustrated wireless access point 22 by suitable digital devices such as an illustrated notebook computer 24, or a desktop computer, or a dumb terminal, or so forth. The accessing digital device provides a display 26 for displaying video and one or more input devices such as an illustrated keyboard 28 and touchpad 29. Medical personnel use the notebook computer 24 or other accessing devices to communicate with the medical server 10. Such medical personnel may include, for example, nurse assistants, nurses, doctors, medical administrative personnel, support or contract workers for a medical or medically related organization, or so forth.

In the illustrated embodiment, the accessing digital device also defines the audio/video recording and playback device 12. The notebook computer 24 includes the display 26 to provide video playback, and typically also includes built-in speakers to provide audio playback. Alternatively or additionally, external speakers (not shown) may be connected with the computer. For recording, an illustrated camera 30 includes a video recording lens 32 and a microphone 34. An indicator light 36 or other indicator optionally activates during recording. In various embodiments, the camera may be integrated into the computer, or may be embodied as a standalone camcorder or so forth. In some embodiments, it may be undesired to have the medical person be video-recorded. In such a circumstance, the video of the medical person can be replaced by a suitable animated virtual avatar simulating a medical professional implemented by a suitable avatar engine 38. (The avatar engine 38 is illustrated diagrammatically, and may for example be physically embodied as software executing on the notebook computer 24, software executing on the server CPU 20, or so forth).

With reference to FIG. 1, the medical server 10 is intended to service a substantial number of chronically ill patients, elderly patients, ill persons, or other end-users. As used herein, the term "patient" is to be broadly construed as encompassing conventional patients in hospitals as well as out-patients, chronically ill persons under continuing out-patient-type medical care for a chronic condition, elderly or frail persons under ongoing medical surveillance through scheduled visits to the doctor's office, or so forth. In one approach, the serviced persons are members of a virtual community that is serviced by the medical server 10. The community members may include, for example, patients of a medical facility, outpatients of a hospital system, nursing home residents, retirees, or so forth who sign up for or otherwise agree to join the virtual medical community. Such a virtual community may be open to anyone who wants to join, or may be restricted to a certain class of members, such as retirees of a sponsoring corporation or patients of a selected medical institution or medical system. The virtual community is a distributed community in which the community members reside in their own homes, or in nursing home residences, or so forth. Each community member has an end-user audio/video recording and playback device 40 operatively connected with the medical server 10 via the Internet 14. Such access is addressed, for example using the IP addresses of the end-user audio/video recording and playback devices 40 as illustrated, so that communication from the medical server 10 can be targeted to specific end-user audio/video recording and playback devices 40. While four end-user audio/video recording and playback devices 40 are illustrated in FIG. 1 as examples, typically the number of end-user audio/video recording and playback devices may number in the dozens, hundreds, or more. Typically, the end-user audio/video recording and playback device 40 are located in the residences (e.g., homes, apartments, nursing home rooms, hospice rooms, retirement community rooms, or so forth) of the associated end-users.

With reference to FIG. 2, to accommodate this substantial number of end-users, a patients database 42 is maintained at the medical server 10. The patients database 42 typically includes address information, such as the illustrated IP addresses, for each end-user audio/video recording and playback device 40. In some embodiments, the patients database 42 further includes care plan schedules 44 that schedule audio/video content or other information to target to each end-user. Thus, for example, an end-user having heart problems may be scheduled for cardiac therapy videos, diet videos, or so forth, while an end-user suffering from diabetes may be scheduled for insulin injection instructional videos, low-salt diet videos, and so forth.

FIG. 2 diagrammatically illustrates the example medical server 10. More generally, the medical server can be embodied by various combinations of hardware and software. For example, in some embodiments a single computer may both host the server and provide user interfacing including embodying the audio/video recording and playback device. In other embodiments, the server may be embodied by a cluster or network of computers, or so forth. Although the single interfacing notebook computer 24 is illustrated as an example, it is contemplated for numerous medical personnel, possibly numbering in the tens, hundreds, or more, to access the medical server 10 via one, two, a few, a few dozen, a few hundred, or more computers or other interfacing digital devices. In some embodiments, some such interfacing computers or digital devices may omit the audio/video recording and playback device, or may omit the recording capability.

With continuing reference to FIG. 1 and with further reference to FIGS. 3A and 3B, an illustrated end-user audio/video recording and playback device 40 is diagrammatically shown as an example. The end-user audio/video recording and playback device 40 differs from the audio-video recording and playback device 12 of the medical server 10 in certain ways that reflect substantial differences between the typical end-user as compared with the typical medical person. End-users tend to be older, more frail (i.e., less healthy), and, as a group, less technically sophisticated than medical personnel. For example, some end-users may be uncomfortable with a computer, or may be unable to operate a computer due to physical or mental limitations. To alleviate these concerns, the illustrated end-user audio/video recording and playback device 40 is built around a consumer entertainment device, such as an illustrated television 50 and DVD player 52. The television 50 may be a standard definition television or a high-definition television, may employ a cathode-ray tube display, LCD display, plasma display, or so forth, and may include built-in audio speakers or be connected with external speakers or an external sound system such as a surround-sound system. The DVD player 52 is optionally omitted, or replaced or supplemented by a video cassette recorder (VCR), a DVD recording device, a digital video recorder (DVR), or so forth. The consumer entertainment device optionally includes other components such as, for example, a gaming machine, cable television box, satellite dish, or so forth.

The end-user audio/video recording and playback device 40 further includes a processor 54 that facilitates interfacing with the medical server 10 via the Internet 14. The illustrated processor 54 is housed in a designated housing such as an illustrated set-top box 56 or other unit, and hence the processor 54 is shown in phantom. In other embodiments the processor may be integrated into the television 50, or integrated into a cable box (arrangement not shown), an Internet interface or gateway, or so forth. The illustrated set-top box 56 also houses a data storage 58, such as an illustrated hard drive again shown in phantom since it is enclosed in the set-top box 56. In other embodiments, the data storage may include a solid state electronic storage medium such as a flash memory, an optical medium such as a recordable optical drive, or so forth.

As is known in the art, consumer entertainment devices such as the illustrative television 50 and DVD player 52 are commonly controlled by one or more hand-held remote controllers. In the illustrated embodiment, a common hand-held remote controller 60 is effective to operate the television 50, the DVD player 52, and the set-top box 56. The hand-held remote controller 60 may be a commercial universal-type remote controller, for example, that is readily configured to control the multiple devices 50, 52, 56. In other embodiments, the hand-held remote controller 60 may be a specially constructed remote controller that, for example, includes extra-large shape-encoded buttons, simplified controls, or so forth, to facilitate ease-of-use by the end-user who may be ill, infirm, have weak eyesight, or be otherwise impaired. Although the illustrated hand-held remote controller 60 is a universal-type remote controller that enables control of all the devices 50, 52, 56, it is also contemplated to have a hand-held remote controller for operating the set-top box 56 that is separate and distinct from one or more other hand-held remote controllers for controlling the consumer entertainment devices 50, 52.

In some embodiments the end-user audio/video recording and playback device 40 is located in the end-user's home, for example in the living room or bedroom. Some end-users may therefore be concerned about personal privacy and security, especially in view of the audio/video recording capability of the end-user audio/video recording and playback device 40. To alleviate these concerns, the recording components are optionally configured to reassure the end-user that recording is not performed surreptitiously or without the end-user's knowledge and control. In the illustrated end-user audio/video recording and playback device 40, a video recording lens 62 includes an automatic lens cover 63 arranged to physically block the video recording lens 62 (as shown in FIG. 3A) except during recording of audio/video content (as shown in FIG. 3B, where the automatic lens cover 63 is automatically moved away to reveal the video recording lens 62). That is, the automatic lens cover 63 is programmed or otherwise interlocked to be open whenever video is being recorded, and to be closed otherwise. By physically blocking the video recording lens 62 from view when it is not in use, the end-user is reassured of his or her privacy. Similarly, a microphone 64 is configured to extend at least partially out of the set-top housing during recording (as shown in FIG. 3B) and retracts into the housing otherwise (as shown in FIG. 3A). While such retraction does not in fact prevent recording, the hiding of the microphone 64 when not in use may nonetheless be reassuring to the end-user.

FIGS. 3A and 3B diagrammatically illustrate the example end-user audio/video recording devices 40. For example, the illustrated embodiment advantageously makes use of the existing television 50. However, it is also contemplated to replace the television by a dedicated replacement consumer entertainment device that integrates the processor, hard drive, and optionally other components into a single housing. While the illustrated video recording lens 62 with automatic blocking lens cover 63 and retractable microphone 64 advantageously reassure the end-user of his or her privacy and security, in other embodiments a recording device without such privacy reassurances is contemplated. On the other hand, it will be appreciated that the automatic blocking lens cover 63 and the retractable microphone 64 will find broader application that is not limited to the disclosed medical communication systems. For example, the automatic blocking lens cover 63 can be usefully employed in any situation where it is advantageous to assure the subject of privacy and security, and may for example be used in cameras for studios that record children, in cameras used for photographing drivers for use on drivers' licenses, and so forth.

With continuing reference to FIGS. 1, 3A and 3B and with further reference to FIG. 4, a typical operation of the illustrated medical communication system is described. Typically, the medical communication system is used to push content from the medical server 10 to targeted end users. Toward this end, based on the care plan schedules 44 the medical server 10 conveys pre-recorded audio/video content 70 targeted to a particular end-user by transmitting the pre-recorded audio/video content 70 to the end-user audio/video recording and playback device 40. For example, in IP/TCP such targeting is suitably achieved by transmitting the pre-recorded audio/video content 70 to the end-user audio/video recording and playback device 40 using the IP address of the device 40 for targeted addressing. Alternatively, the pre-recorded content may be stored on the set-top box 56 of the targeted end-user, and the medical server 10 conveys an identification of the portion of such pre-recorded content to be presented.

The selection of pre-recorded audio/video content 70 is selected based on the care plan schedule 44 to relate to health concerns, issues, wellness, or the like pertaining to the targeted end-user. For example, if the end-user has heart problems, the pre-recorded audio/video content 70 may include exercise videos, diet lessons, instructions on taking medications, or so forth. The pre-recorded audio/video content 70 may also include encouragement messages. In some embodiments, the pre-recorded audio/video content 70 is interactive in a structured way. For example, the pre-recorded audio/video content 70 may include an interactive survey which the end-user answers by inputting responses using the hand-held remote controller 60, and these structured responses are sent back to the medical server 10 via the Internet 14.

At the end-user audio/video recording and playback device 40, the transmitted pre-recorded audio/video content 70 is stored, for example on the hard disk 58, and played back at the end-user's request. In a suitable approach, the processor 54 provides a graphical user interface in cooperation with the television 50 which enables selective playback of pre-recorded audio/video content 70 received from the medical server 10. For example, the processor 54 may be programmed to receive the pre-recorded audio/video content 70 at night when Internet usage is low, and stores received pre-recorded audio/video content 70' on the hard drive 58. (In this description, primed reference numbers indicate received audio/video material). The user then turns on the television 50 and selects the medical graphical user interface using suitable power and select buttons on the hand-held remote controller 60. In response, the processor 54 causes the television 50 to display a menu of textual and optionally graphical items including a list of audio/video offerings including at least the received pre-recorded audio/video content 70'.

The pre-recorded audio/video content 70, 70' is principally one-way (i.e., server-to-end user), with optional structured responses such as survey responses optionally communicated from the end-user back to the medical server 10. However, it in some circumstances the end-user may want to send unscheduled or unstructured responses. For example, the end-user may be experiencing a new physiological symptom (e.g., pain, numbness, lack of appetite, or so forth) that the end-user wants to report to medical personnel. As another example, after seeing a diet video the end-user may have questions regarding the permissibility of certain foods.

Accordingly, the end-user may initiate an inquiry 80. In some embodiments, the inquiry 80 may be a general inquiry to be answered by any medical personnel who are available at the medical server 10. In other embodiments, the inquiry 80 may be specifically addressed to a particular medical person, such as a nurse assigned to the end-user. The inquiry 80 is suitably generated by accessing the graphical user interface. For example, the processor 54 may generate a graphical selection option (e.g., a button or so forth) labeled, for example, "Send video message to Nurse Jones", and the end-user generates the inquiry 80 by selecting that option using the hand-held remote controller 60. The inquiry 80 may be addressed to a specific medical person (e.g., Nurse Jones) or to a group of medical personnel (e.g., using a selection option labeled "Send video message to the Nurse on call"). The inquiry 80 is sent via the Internet 14 and received at the medical server 10, where a decision 82 is made as to whether a suitable medical person is available in real time to field the inquiry.

If an addressed medical person is available in real time, then optionally an audio/video conference or real-time video call 84 is initiated between the end-user associated with the initiating end-user audio/video recording and playback device 40 that sent the inquiry 80 and the medical professional. This is suitably implemented at the medical server 10 by displaying the audio/video content of the video call 84 on the computer 24, and is suitably implemented at the initiating end-user audio/video recording and playback device 40 by displaying the audio/video content on the television 50, either in a full-screen mode or in a window, picture-in-picture display region, or other limited region of the display of the television 50. Audio is suitably provided through the built-in television speakers or through external speakers or an external sound system operatively connected with the television 50.

On the other hand, if no suitable medical personnel are available in real time to field the inquiry 80, then the initiating end-user audio/video recording and playback device 40 is informed of this. In response, the initiating end-user audio/video recording and playback device 40 records an audio/video message 90 that is transmitted via the Internet 14 (diagrammatically indicated in FIG. 1 by arrow 92 in FIGS. 1 and 4 for an audio/video message sent by the end-user device with IP address #2) to the medical server 10. The video recording is suitably performed by the video recording lens 62 with the automatic blocking lens cover 63 opened as in FIG. 3B to reveal the lens 62 (thus emphatically informing the end-user that recording is engaged) and the audio recording is suitably performed by the retractable microphone 64 in its extended position as shown in FIG. 3B (again, emphatically informing the end-user that recording is engaged). The end-user suitably presses a selected button of the remote control 60 to start and stop the recording. Optionally, after recording is complete the graphical user interface provides an option for the end-user to playback the recorded audio/video message 90 on the television 50 before sending. If it is unsatisfactory, the end-user can delete the recorded audio/video message 90 and optionally record a new version. Once the end-user is satisfied with the recorded audio/video message 90, the end-user selects a "Send" option or other suitably labeled control of the graphical user interface, and the processor 54 sends the recorded audio/video message 90 to the medical server 10, with suitable addressing information such as an IP address, email address, MAC address, or so forth.

At the medical server 10, the received audio/video message 90' is stored and played back. For example, the received audio/video message 90' is typically stored, until an appropriate medical person becomes available in real-time to field the inquiry. Optionally, the received audio/video message 90' is stored in the patient's data file, so as to be referenced by the patient's doctor or other medical personnel for diagnostic or when designing the care plan schedules 44, or so forth. For example, the central processing unit (CPU) 20 suitably implements an audio/video handling and routing system that accepts the incoming received audio/video message 90', stores a copy of the received audio/video message 90' in the patient's electronic file in the electronic database 42, and routes a copy of the received audio/video message 90' to a received video messages queue for playback by the next available medical person, or routes a copy of the received audio/video message 90' to a video mailbox of the medical person to which the audio/video message 90' is addressed, if such addressing information is included with the message.

When a suitable medical person becomes available, he or she plays back the received audio/video message 90', for example on the notebook computer 24. The playback at the medical server 10, or more specifically at the computer 24, can use dedicated playback software. However, since the medical person is typically relatively knowledgeable about computers, it is also contemplated to have the received audio/video message 90' forwarded to the medical professional as an email attachment, which the medical professional plays back by routine manipulations performed in the medical professional's email reading program (possibly operating in conjunction with a plug-in or other associated software such as a media player program).

Preferably, the medical person records an audio/video response 94, for example using the camera 30, and the recorded audio/video response 94 is transmitted via the Internet 14 (diagrammatically indicated in FIG. 1 by arrow 96 in FIGS. 1 and 4 for an audio/video response sent back to the end-user device with IP address #2) to the initiating end-user audio/video recording and playback device 40, where it is stored as a queued audio/video response 94' and played back at the convenience of the end user. For example, the graphical user interface suitably lists the received audio/video response that can be selected for playback by the end-user using the handheld remote control device 60.

The illustrated embodiment includes the option of the real-time video call 84 which is used if a suitable medical person is available in real time when the inquiry 80 is made. In other embodiments, the option of a real-time video call is omitted (along with omission of the decision 82), and every inquiry is made as an audio/video message and every response is made as a recorded audio/video response. It is also contemplated for the decision 82 to employ different criteria or timing; for example, it is contemplated to always record the audio/video message, and to initiate the video call only at the medical person's option. In such an embodiment, for example, the medical person may review the audio/video message. If it is non-urgent, then a recorded audio/video response is appropriate. On the other hand, if the audio/video message indicates a possibly urgent problem such as a medical symptom that may indicate a medical condition requiring rapid intervention, then the medical person can initiate the video call.

Advantageously, the audio/video message 90, 90' enables the end-user to convey non-verbal information by gestures and so forth. Indeed, some such non-verbal communication may be unintended—for example, the receiving medical person may be able to discern aspects of the end-user's condition from the video. For example, the end-user may appear pale, or thin, or disoriented. As another option, if the patient believes a medical emergency may be imminent, the patient can leave the camera "on" so that the medical person who video calls back can see that the patient has passed out or is otherwise unable to respond. These are all substantial advantages over the conventional audio-only telephonic message used heretofore.

Typically, the audio/video response 94, 94' employs the video recording lens 32 of the camera 30 to record video of the responding medical person. This approach advantageously provides the end-user with personal contact which can counteract loneliness or depression. In some embodiments, however, it is contemplated for the avatar engine 38 to produce the video portion of the audio/video response 94, 94' as an animated avatar simulating a medical professional in the generated audio/video responses 94, 94'. Such an avatar is suitably substituted for recording video of the responding medical person. One situation in which an animated avatar may be advantageous is where the medical server 10 is staffed by different medical personnel at different times. For example, a busy medical server may employ a bank of responders, such that each time a given end-user sends an audio/video message a different medical person may in general respond. In such a case, the avatar provides a consistent interface. In some other embodiments, video of the medical person is recorded, but the background is configured to provide a more patient-comforting setting. For example, rather than having the medical person shown in his or her actual environment, such as a hospital with other medical personnel moving about, a replacement background can be inserted by suitable digital video processing to show the medical person in a quiet doctor's office, a library, interview room, or other more comforting setting.

The systems and methods described with reference to FIG. 4 are also readily adapted for use as a medical emergency alert system or method. In such embodiments, the medical center is a continuously staffed medical emergency center staffed by nurses or other medical personnel trained to respond to medical emergencies by calling 911, acquiring medical information from the caller, or taking other such emergency measures as appropriate. In these embodiments, most calls are processed by the available emergency responder (corresponding to the illustrated available nurse 82 in FIG. 4) by a real-time video call 84. However, if the medical emergency center is overloaded (that is, attempts to process more calls at the same time than there are emergency responders) then the message is logged as audio/video message 90, 90' and stored until the next available emergency responder is available. For such an emergency response system, the received message 90' should be automatically flagged with the MAC address or other address of the sending audio/video device so that the emergency responder can quickly get back to the caller. Moreover, in such an emergency response system the residence-end hardware illustrated in FIGS. 3A and 3B (including the consumer electronics devices 50, 52 and the set-top box 56) is suitably replaced by a more compact, preferably portable system such as a battery-powered audio/video recording and playback device that connects with the Internet 14 or another network via a wireless card or other wireless link. A cellular telephone with video call capability is one suitable portable audio/video device—in this case the Internet 14 is suitably replaced by the cellular telephone network, and addressing is by telephone number. The user can readily program the telephone number of the emergency center as a quick-dial number (for example, dialed upon pressing "1" followed by "Send") so that in an emergency the user can quickly query the emergency response system. Such emergency response systems have certain advantages over existing telephonic emergency response systems in that the person experiencing the emergency is reassured by seeing an actual person instead of merely receiving a telephonic voice response, and the emergency responder can better assess the person's condition based on visual appearance and visually perceptible behavior.

With reference to FIG. 5, in some embodiments a microphone 164 is disposed on the handheld remote controller 60, and the microphone 164 substitutes for the microphone 64 on or in the set-top box 56. To enable transmission of audio recorded by the microphone 164, the remote controller 60 suitably includes an audio transmitter 166 to transmit the audio picked up by the microphone 164 to the set-top box 56. The output of the microphone 164 may be transmitted to the set-top box 56 in analog form, or may be first digitized by processing (not shown) in the handheld remote controller 60 and then transmitted to the set-top box 56 by a the transmitter 166 which in such embodiments may be, for example, a Bluetooth transmitter. The transmitted audio is thenceforth processed at the set-top box 56 and transmitted across the Internet 14 to the medical server 10 in the same way as the audio recorded by the microphone 64.

The transmitter 166 for transmitting the picked up audio may be the same as, or different from, the transmitter used to transmit indications operation of the buttons 168 or other tactile controls of the remote controller 60. For example, the audio transmitter 166 may be a Bluetooth or radio frequency transmitter, while button operation may be transmitted using a pulsed infrared transmitter. It is also contemplated for the built-in microphone 164 to be configured to enable the patient to convey voice commands to the set-top box 56, or to the television 50, DVD 52, or other consumer entertainment device 50, 52 controlled by the remote controller 60. Such audio command capability, utilizing suitable voice recognition software executing on the handheld remote controller 60 or at the set-top box 56 or other receiving device 50, 52, 56, can be particularly convenient for certain patients who may have limited manual dexterity.

An advantage of the microphone 164 over the set-top box microphone 64 is that the user can hold the microphone 164 close to his or her lips during recording. Since the microphone 164 is built into the hand-held remote controller 60, it is assured that the microphone is readily available to the patient as he or she uses the medical communication system. In the case of a frail person with a weak voice, having the microphone 164 built into the remote controller 60 may be more convenient and may produce a better quality audio recording as compared with using the relatively more remote set-top microphone 64.

In some embodiments, the microphone 164 is used for audio-only recording, either as an additional function or as a substitute function for the described video messaging. For example, as an additional function the microphone 164 can be used to record a voice message for medical personnel. In some such embodiments, a voice-over-Internet protocol (VOIP) is used to send the message and store it at the server 10 until it is retrieved and played back by medical personnel. For example, the patient may press a "Help Desk" button 170 to indicate that he or she wishes to send a voice message to a nurse or other medical person at the server 10. Alternatively, suitable voice recognition capability may be built into the remote 60 or the set-top box 56 so as to recognize a suitable verbal initiation command such as "help desk" or "record". The system suitably responds by informing the patient (for example, via a display on the television 50) that he or she should hold down the "Help Desk" button 170 and speak into the microphone 164 to record the message. The message may be transmitted in real-time by a VOIP to the server 10, or may be recorded locally at the set-top box 56 and then transmitted.

An advantage of the illustrative voice messaging using the microphone 164 is that it allows the patient to send a one-way message to medical personnel. The patient may prefer this to the alternative of discussing the issue with a medical person in real time. In an example, a patient may be using the medical communication system when the patient receives an invitation from a friend to go on a fishing trip the next day, which would conflict with a survey scheduled by the patient's care plan 44. The patient suitably presses the "Help Desk" button 170 and the microphone 166 is activated. The patient leaves a voice message with the help desk indicating that the patient was scheduled to participate in a survey tomorrow, but that the patient wants to reschedule one day later. It will be noted that the patient does not need to explain this change of plan or argue with a nurse about rescheduling, because the voice message is a one-way message from the patient's side. The set top box 56 switches to a helpdesk mode or otherwise establishes the VOIP or other suitable connection to the server 10 for recording voice message. As the patient talks into the microphone 164, the set top box 56 passes the continuous voice streams of the patient (in the case of real-time VOIP communication) to the server 10 where the patient's voice is recorded and stored for later retrieval. When finished, the patient switches to normal usage mode (or, alternatively, such a switch is made automatically). The voice message is stored at the server 10 as a voice message or other distinguishable audio file. A helpdesk employee preferably checks the voice mail or other help desk audio repository at a regular interval to play back any queued audio messages, via a convenient user interface such as the speakers of the computer 24. The employee listens to the voice message and may, for example, decide that it is acceptable to re-schedule the survey for the next day. The employee suitably uses information stored on the server 10 to make this decision. On the other hand, if the patient's request or information is more critical (such as, for example, informing the help desk that the patient plans to double the dosage of his or her medication) then the employee may forward the message to the patient's doctor or another person qualified to respond. The employee may optionally send a responsive voice or video message back to the patient.

The illustrated embodiment of the help desk employs the built-in microphone 164 and the Internet 14. However, another audio recording device can be used instead, such as the set-top box microphone 64. Similarly, another communication pathway can be used, such as a cellular telephone network.

The invention claimed is:

1. An apparatus comprising:
   a handheld remote controller for controlling an electronic audio/video recording and playback device, the handheld remote controller including tactile controls for entering control commands;
   a built-in microphone built into the handheld remote controller;
   a transmitter for transmitting audio picked up by the built-in microphone from the handheld remote controller; and
   a medical server configured to cause the electronic audio/video recording and playback device controlled by the handheld remote controller to play back pre-recorded medically related content, the microphone being configured to convey audio from the patient to the patient audio/video recording and playback device.

2. The apparatus as set forth in claim 1, wherein the transmitter for transmitting audio picked up by the built-in microphone is not used to transmit control commands entered using the tactile controls.

3. The apparatus as set forth in claim 1, wherein the medical server contains storage for storing a voice message recorded by the patient using the built-in microphone for later playback by medical personnel.

4. The apparatus as set forth in claim 1, wherein the electronic audio/video recording and playback device includes a television.

5. An apparatus comprising:
   a handheld remote controller for controlling a television, DVD, set-top box, or other electronic device, the handheld remote controller including tactile controls for entering control commands;
   a built-in microphone built into the handheld remote controller;
   a transmitter for transmitting audio picked up by the built-in microphone from the handheld remote controller; and
   a medical server configured to cause a patient audio/video recording and playback device controlled by the handheld remote controller to play back pre-recorded medically related content, the microphone being configured to convey audio from the patient to the patient audio/video recording and playback device.

6. The apparatus as set forth in claim 5, wherein the medical server contains storage for storing a voice message recorded by the patient using the built-in microphone for later playback by medical personnel.

7. The apparatus as set forth in claim 5, wherein the transmitter for transmitting audio picked up by the built-in microphone is not used to transmit control commands entered using the tactile controls.

8. The apparatus as set forth in claim 5, wherein the television, DVD, set-top box, or other electronic device includes a television.

9. An apparatus comprising:
   an electronic audio/video recording and playback device including a consumer entertainment device;
   a handheld remote controller configured to control at least one component of the consumer entertainment device via tactile controls for entering control commands, the handheld remote controller further including:
      a built-in microphone, and
      a built-in transmitter configured to transmit audio picked up by the built-in microphone from the handheld remote controller to the electronic audio/video recording and playback device; and
   a medical server configured to interface with the electronic audio/video recording and playback device controlled by the handheld remote controller to play back pre-recorded medically related content;
   wherein the electronic audio/video recording and playback device is configured to transmit audio picked up by the built-in microphone across the Internet to the medical server.

10. The apparatus as set forth in claim 9 wherein the consumer entertainment device includes a television and the handheld remote controller is configured to control at least the television via the tactile controls.

11. The apparatus as set forth in claim 10, wherein the consumer entertainment device further includes at least one additional component in addition to the television, the at least one additional component including one or more of: a DVD player, a video cassette recorder (VCR), a gaming machine, a cable television box, and a satellite dish.

12. The apparatus as set forth in claim 10, wherein the consumer entertainment device further includes one or more additional components in addition to the television, and the handheld remote controller is a universal-type handheld remote controller configured to control all components of the consumer entertainment device.

13. The apparatus as set forth in claim 9, wherein:
   the handheld remote controller is configured to transmit a voice message to the electronic audio/video recording and playback device; and
   the electronic audio/video recording and playback device is configured to transmit the voice message to the medical server.

14. The apparatus as set forth in claim 9, wherein:
   the handheld remote controller and the audio/video recording and playback device are configured to transmit a video message across the Internet to the medical server.

15. The apparatus as set forth in claim 9, wherein the medical server is configured to interface with the electronic audio/video recording and playback device to:
   transmit medically related content stored at the medical server across the Internet to the electronic audio/video recording and playback device; and
   wherein the transmitted medical related content is played back by the electronic audio/video recording and playback device.

16. The apparatus as set forth in claim 15, wherein the handheld remote controller and the audio/video recording and playback device are configured to transmit a message received via at least the built-in microphone of the handheld remote controller across the Internet to the medical server.

17. The apparatus as set forth in claim 9, wherein the handheld remote controller and the audio/video recording and playback device are configured to transmit a message received via at least the built-in microphone of the handheld remote controller across the Internet to the medical server.

18. An comprising:
   an electronic audio/video recording and playback device including a consumer entertainment device;
   a handheld remote controller configured to control at least one component of the consumer entertainment device via tactile controls for entering control commands, the handheld remote controller further including a built-in microphone and a built-in transmitter configured to transmit audio picked up by the built-in microphone from the handheld remote controller to the electronic audio/video recording and playback device, wherein the transmitter of the handheld remote controller is configured to digitize audio picked up by the built-in microphone and transmit the digitized audio from the handheld remote controller to the electronic audio/video recording and playback device; and
   a medical server configured to interface with the electronic audio/video recording and playback device controlled by the handheld remote controller to play back prerecorded medically related content.

\* \* \* \* \*